United States Patent

Köster et al.

[11] 4,010,204
[45] Mar. 1, 1977

[54] PROCESS FOR PREPARING CONDENSATION PRODUCTS

[75] Inventors: Roland Köster; Ali-Akbar Pourzal, both of Mulheim (Ruhr), Germany

[73] Assignee: Studiengesellschaft Kohle m.b.H., Mulheim (Ruhr), Germany

[22] Filed: Nov. 13, 1974

[21] Appl. No.: 523,283

Related U.S. Application Data

[63] Continuation-in-part of Ser. No. 523,285, Nov. 13, 1974, abandoned.

[52] U.S. Cl. .......... 260/586 C; 260/590 E; 260/593 R; 260/598; 260/599; 260/601 R
[51] Int. Cl.² ............ C07C 45/00; C07B 5/02
[58] Field of Search .......... 260/586 C, 593 R, 590, 260/591, 592, 598, 601 R, 599

[56] References Cited

UNITED STATES PATENTS

| | | | |
|---|---|---|---|
| 2,309,650 | 2/1943 | McAllister et al. | 260/593 R |
| 2,393,510 | 1/1946 | Bailey et al. | 260/586 C |
| 2,429,361 | 10/1947 | Linn et al. | 260/586 C |
| 2,431,754 | 12/1947 | Spatieff et al. | 260/586 C |
| 2,549,508 | 4/1951 | Mottern | 260/593 R |
| 2,549,520 | 4/1951 | Prichard | 260/586 C |
| 2,719,863 | 10/1955 | Haslan | 260/586 C |
| 3,248,428 | 4/1966 | Porter et al. | 260/593 R |
| 3,542,878 | 11/1970 | Swift | 260/586 C |
| 3,728,087 | 4/1973 | Stapfer et al. | 260/586 C |
| 3,829,495 | 8/1974 | Mitzutani | 260/586 C |

Primary Examiner—Norman Morgenstern
Attorney, Agent, or Firm—Burgess, Dinklage & Sprung

[57] ABSTRACT

A condensation according to the following equation

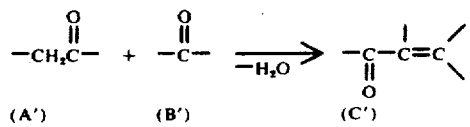

is carried out in the presence of a dialkyl boryl carbonxylate, e.g. diethyl boryl pivalate. High yields are obtained.

8 Claims, No Drawings

PROCESS FOR PREPARING CONDENSATION PRODUCTS

This application is a continuation-in-part of Ser. No. 532,285, filed Nov. 13, 1974, now abandoned.

In application in which one of us is an applicant, Ser. No. 297,146, filed Dec. 10, 1972, dialkyl boryl carboxylates are employed in the protolyses of trialkyl boranes and compounds containing protons.

This invention relates to a process for the production of aldol condensates and in particular a process for the production of substituted vinyl ketones and vinyl aldehydes with the use of novel condensing agents.

In accordance with the invention, carbonyl compounds $RCH_2COR'$ (A) wherein R is H, alkyl or aryl and R' is hydrogen, alkyl or aryl are condensed with themselves (reaction type I) or with other carbonyl compounds $R''COR'''$ (B) wherein R'' and R''' are H, alkyl or aryl (reaction type II) to form condensation products (C). R and R', or R'' and R''', or R' and R''', or R' and R'', or may also be linked together.

The condensing agents used for the reactions are dialkyl boryl carboxylates having the general formula $R_2{}^V BOCOR^{IV}$ wherein $R^{IV}$ stands for $C_1$–$C_6$ hydrocarbons and $R^V$ for $C_1$–$C_4$ hydrocarbons. The use of the liquid diethyl boryl pivalate ($R^V$ = ethyl; $R^{IV}$ is t-butyl) is particularly advantageous, but also the other, e.g., solid diethyl boryl carboxylates, e.g., from acetic acid, butyric acid, 3,3-dimethyl butyric acid, cyclopropane carboxylic acid and benzoic acid may be used.

The condensations of A and B by means of the dialkyl boryl carboxylates used in accordance with the invention are described by the general equation (a):

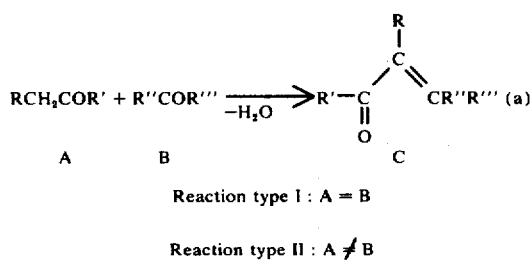

Reaction type I : A = B

Reaction type II : A ≠ B

The cleavage of water corresponds to the reaction of the dialkyl boryl carboxylates according to the equation (b), e.g.,

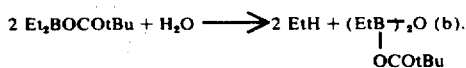

The oxides produced of the equation (b) are generally readily separated. The solid bis-[ethyl-pivaloyloxy-boryl]-oxide can be distilled off particularly readily. Moreover, its filtration to separate it is also well suited.

The carbonyl compounds of the type A are capable of reacting with themselves (reaction type I). In accordance with the invention, ketones and aldehydes having one alpha-$CH_2$ group or ketones having two alpha-$CH_2$ groups as well as diketon and keto aldehydes having one to three alpha-$CH_2$ groups are suitable as component A:

$RCH_2COR'$, e.g., with R = hydrogen or alkyl such as methyl, ethyl propyl, butyl and R' = R or isopropyl, t-butyl, phenyl, subst. phenyl (o-, p-, m-methyl, chlorine, hydroxyl, acetoxy, amino)

$RCH_2COCH_2COCH_2R'$, e.g., with R = hydrogen
R' = hydrogen

The ketoaldehyde $RCH_2COCH_2C(O)H$ can also be used.

One mole of the component B reacts per 1 mole of alpha-$CH_2$ groups of A. Suitable A components also include cyclic ketones (linkage of R and R') of various ring sizes $OC(CH_2)_n$ wherein n is 4 to 15 and more. Purely aliphatic ring ketones such as cyclopentanone (n = 4) or cyclopentadecanone (n = 14) and unsaturated ring ketones (2-cyclohexenone and isophorone) a also well suited for the process according to the invention. The A components may also bear various substituents on R or R'. Sterically rigid ketones such as camphor or norbornanone may also be used for the purposes of the invention.

Particularly useful as B component for the reaction type II are the non-enolizable aldehydes and ketones. For example, benzaldehyde, pivaladehyde, benzophenone, adamantano fluorenone, and benzylidene acetophenone have been found to be suitable.

In the reactions of the type II, linking of the compound A with a plurality of compounds B may also occur according to the invention if the component A contains two or more alpha-$CH_2$ groups. Diketones such as diacetyl, dimedone or acetyl acetone react in a completely analogous manner as A component. Finally, the resultant compounds of the type C may also further react as A or B components according to the process of the invention, in the case of A, if they contain vinylogous alpha-$CH_2$ groups, in which case in C (equation (a)), R''' is $CH_2R^{VI}$.

The reactions in accordance with the invention proceed at atmospheric pressure or reduced or elevated pressures, and, in most cases, commence at as low as 20° or above 20° C. Above 80° C, the reaction rate is high. The temperature range between 80° and 150° C. is optimum. The exothermic reactions then lead smoothly and almost quantitative to the compounds of the C type. These are generally obtained directly in pure form or as E/Z isomer mixture (E = opposite, Z = same side according to the directives of IUPAC nomenclature). Additional purification may be effected, for example, by boiling up for a short period of time in methanol. However, distillation or recrystallization are not necessary for purification in most cases.

The reactions can also be readily carried out in various solvents such as aliphatic or aromatic hydrocarbons or in ethers or halogenated hydrocarbons. Toluene or xylene are very useful for obtaining crystalline condensation products C.

As compared with the previously usual possibilities of aldol condensations, the reactions according to the invention offer substantially more possibilities of C—C linkage. By means of the process, also unsaturated carbonyl compounds such as cyclohexenone can be readily condensed. Moreover, markedly higher yields as compared with those obtained with known condensing agents are obtained. Functional groups such as, for example, chlorine, hydroxyl or amino groups do not interfere. For example, high yields of dimers of acylophenones which are appropriately substituted in the phenyl nucleus are obtained. Additionally, the products always are of substantially higher purity than those obtained with the use of the previously usual condensing agents.

The following summary of the condensates C which are obtainable according to the invention by reaction type I and reaction type II illustrates the possible variations of the process according to the invention.

(1) Homocondensates C of the reaction type I (A = B)

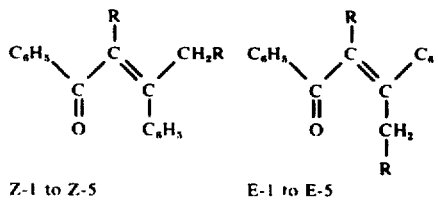

Z-1 to Z-5    E-1 to E-5

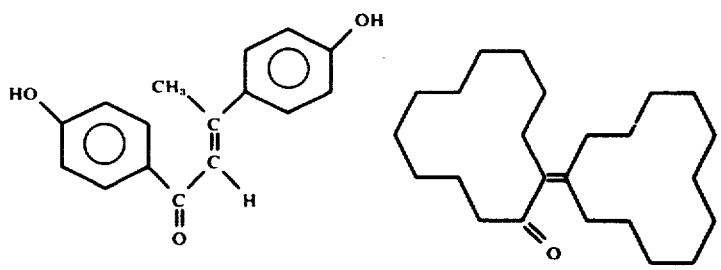

E-8    11

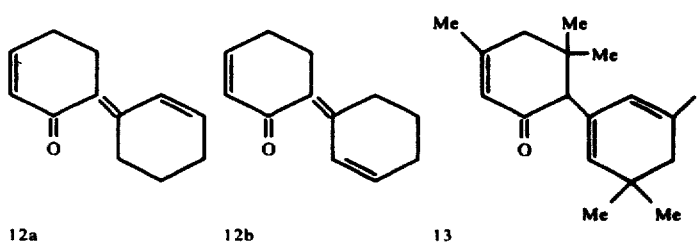

12a    12b    13

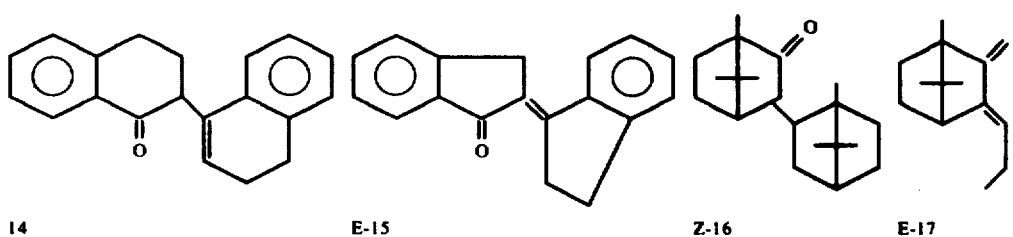

14    E-15    Z-16    E-17

(2) 1:1, 1:2, and 1:3 cocondensates C of the reaction type II (A ≠ B)

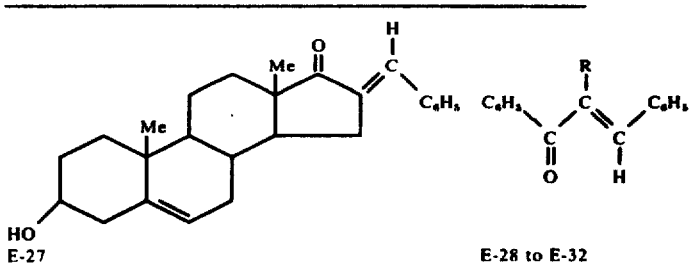

E-27    E-28 to E-32

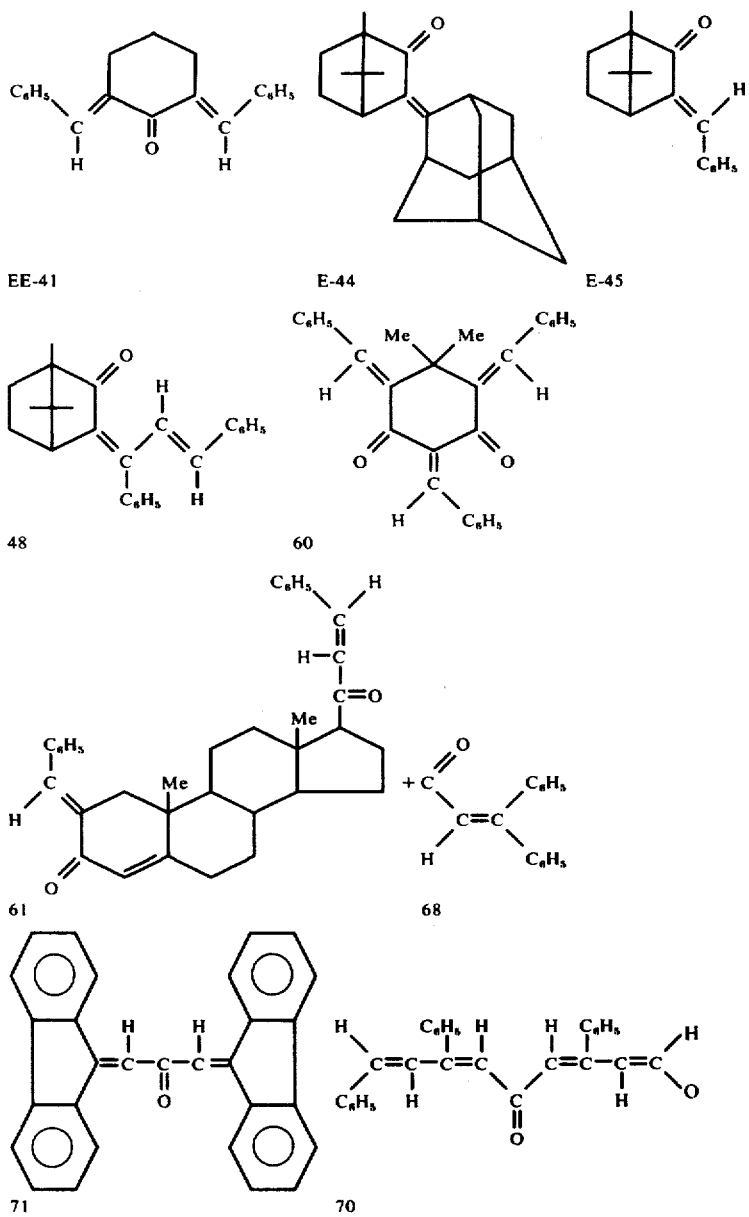

EXAMPLES

Condensation by the reaction type I (A = B)

Dimeric condensation products from alkyl phenyl ketones (see Tables 1 and 2)

5-Benzoyl-6-undec-5-en (Z/E) from caprophenone:

Diethyl boryl pivalate (33.4 g., 197 mmoles) is added dropwise at 90° C. within about 2 hours to 1-oxo-1-phenylhexane (caprophenone; 34.5 gram mmoles) while stirring. While the mixture turns faintly yellow, ethane is evolved (4.36 std.liters 99%). Thereafter bis-[ethyl-pivaloyl-oxy-boryl]-oxide (28.2 g., 97%) is distilled off in vacuum from the clear yellowish liquid. residue is mixed with methanol (100 ml.) and all readily volatile constituents are distilled off. A Z/E isomer mixture is isolated as a liquid yellowish borine-free residue. Yield, 31.3 g (95%); purity (by gas chromatography) 97%.

Table 1

| Dimeric condensation products from alkyl phenyl ketones (Acylophenones) | | | | |
|---|---|---|---|---|
| | Dimeric condensates 1 to 5 | | | |
| Alkyl phenyl ketone | Yield (%) | Purity (%) | Characteristic | Consecutive No. |
| Acetophenone | 72[a] | 98 | liquid, yellow | 1 |
| Propiophenone | 97 | 98 | liquid, yellowish | 2 |
| Butyrophenone | 96 | 99 | liquid, yellowish | 3 |
| Valerophenone | 96 | 96 | liquid, yellowish | 4 |

Table 1-continued

Dimeric condensation products from alkyl phenyl ketones (Acylophenones)

| Alkyl phenyl ketone | Dimeric condensates 1 to 5 | | | |
|---|---|---|---|---|
| | Yield (%) | Purity (%) | Characteristic | Consecutive No. |
| Caprophenone | 95 | 97 | liquid, yellowish | 5 |

*The residue consists of trimeric and tetrameric condensates depending upon the mode of operation.

Table 2

| Substituted Acetophenone | Dimeric condensates from substituted acetophenones | | | |
|---|---|---|---|---|
| | Dimeric condensates 6-9 | | | |
| | Yield (%) | Purity (%) | Characteristic | Consecutive No. |
| 2-Chloroacetophenone | 82 | 92 | viscous, green | 6 |
| 4-Acetoxy-acetophenone | 74 | >95 | liquid, orange | 7 |
| 4-Hydroxy-acetophenone | 77 | >95 | solid brown powder | 8 |
| 2-4-Dimethyl-acetophenone | 73 | 99 | liquid, yellow | 9 |

Dimeric condensates C by reaction type 1 from cyclic ketones (see Table 3)

To 18.2 g. (100 mmoles) of cyclododecanone in 100 ml., of toluene are added dropwise at 100° C. within about 50 minutes 17.7 g. (104 mmoles) of diethyl boryl pivalate. 2.58 Std.liters (115 mmoles) of ethane (MS) are cleaved off. After the diluent, 15.9 g. (53 mmoles) of bis(ethyl-pivaloyloxyboryl)oxide having a boiling point of 55°–60° C/0.1 mm are distilled off from the solid white mixture to give 16.2 g. of a white crystalline residue (found, 0.2% B). After boiling-up in 100 ml. of methanol, the readily volatile constituents are distilled off to give 15.5 g. (44.8 mmoles) of a condensate having a melting point of 132°–134° C.

To 14.5 g. (109.3 mmoles) of indanone are added dropwise at 100° to 110° C. within about 1 hour 18.2 g. (107 mmoles of diethyl boryl pivalate. While the mixture assumes a faint yellowish color, 2.15 std.liters (96 mmoles) of ethane (MS) are evolved. The mixture solidifies when allowed to cool. Vacuum distillation gives 14.5 g. (49 mmoles) of bis(ethylpivaloyloxyboryl)-oxide having a boiling point of 48°-75° C./0.1mm and 13.5 g. of raw condensate as a solid residue. After washing with heptane, 12.8 g. (52.3 mmoles) of condensate having a melting point of 126° to 129° C. are obtained.

Table 3

| Cycloketone | Dimeric condensates from cyclic ketones | | | |
|---|---|---|---|---|
| | Dimeric condensates 10-16 | | | |
| | Yield (%) | Purity (%) | Characteristic | Consecutive No. |
| Cyclooctanone | 92 | 95 | liquid, yellowish | 10 |
| Cyclododecanone | 90 | 95 | solid, white, m.p. 132–134° C | 11 |
| 2-Cyclohexenone | 91 | 99 | liquid, yellow | 12 |
| Isophorone | 89 | 99 | viscous, yellow | 13 |
| 1-Tetralone | 90 | 100 | solid, yellowish m.p. 132–133° C. | 14 |
| 1-Indanone | 96 | 99 | solid, yellowish m.p. 126–129° C | 15 |
| Camphor* | 89 | 98 | solid, white m.p. 55–56° C. | 16 |

*At 150° C. about 50% conversion in 4 hours.

Dimeric condensates C by reaction type 1 from steroid ketones (see Table 4)

General prescription:

3 to 5 Millimoles of steroid ketone in a 3- to 4 fold excess of diethyl boryl pivalate are heated for about 30 minutes without a diluent or in the presence of about 50 ml. of xylene to 120°–130° C. While heating, 6 to 10 mmoles of ethane (MS) are evolved. Thereafter the readily volatile constituents are distilled off using finally vaccum of 0.1 Torr (bath of 100° C.). The residue is mixed with 50 ml. of methanol. After having removed the borin-containing constituents by distillation (bath of 100° C., 0.1 Torr), the corresponding crystalline condensates are obtained.

Table 4

| Ketone | Dimeric Condensates 17-20 | | | |
|---|---|---|---|---|
| | Yield (%) | Purity (%) | Characteristic | Consecutive No. |
| Androsterone | 97 | >95 | solid, colorless m.p. >220° C. | 17 |
| Epiandrosterone | 95 | >95 | solid, colorless m.p. >220° C. | 18 |
| Dehydro-epiandrosteron | 95 | >95 | solid, colorless m.p. >220° C. | 19 |
| Testosterone | 98 | >95 | solid, yellow m.p. >220° C. | 20 |

Condensation by reaction type II (A ≠ B) Benzaldehyde and ketones with an alpha-CH$_2$ group (see Table 5)

General prescription:

To a mixture of 30 to 80 mmoles of ketone and 40 to 100 mmoles of benzaldehyde are added dropwise at about 120° C. while thoroughly stirring 60 to 160 mmoles of diethyl boryl pivalate. While the liquid mixture changes its color, 60 to 160 mmoles of ethane with at most 1 to 5% of ethylene are evolved. The mixture is maintained at 20° C for further 30 minutes until gas evolution has ceased. Then by distillation 10 to 20mmoles of excess benzaldehyde are removed and afterwards by vacuum distillation 30 to 80 mmoles of bis(ethyl-pivaloyloxy-boryl)oxide boiling at 65° to 85° C/0.1 Torr. The residue (30 to 80 mmoles) is mixed with about 100 to 200 ml of methanol. The boron-containing constituents and traces of pivalic acid are finally removed by vacuum distillation (0.1 Torr). Solid condensates can be recrystallized from methanol or heptane.

Dehydroepiandrosterone and benzaldehyde:

From 2.8 g. (9.7 mmoles) of hormone, 2 g. (18.9 mmoles) of benzaldehyde, and 5.5 g. (32.3 mmoles) of diethyl boryl pivalate there after 15 min. are obtained 663 std.ml (29.6mmoles of pure ethane (MS) and 2.7 g. (9.06 mmoles) of bis(ethylpivaloyloxy-boryl)oxide. After having mixed the yellow residue with 50 ml. of methanol, 3.5 g. (9.3 mmoles) of condensate having a melting point of 164° C. are isolated.

1-Tetralone and benzaldehyde:

From 5.6 g. (33.4 mmoles) of tetralone, 4.1 g. (38.7 mmoles) of benzaldehyde, and 11.9 g. (70 mmoles) of diethyl boryl pivalate there after 1 h are obtained 1.62 std.liters (72.3 mmoles) of pure ethane (MS) and 9.7 g. (33 mmoles) of bis(ethyl-pivaloxy-boryl)oxide. From the orange residue are obtained with 2 × 50 ml. of methanol 7.5 g. (32.1 mmoles) of 97% (GC) yellow E condensation having a melting point of 96° C.

2-Cyclohexenone and benzaldehyde 6.6 Grams (68.7 mmoles) of cyclohexanone, 8.7 g. (82.1 mmoles) of benzaldehyde and 24.5 g. (144.2 mmoles) of diethyl boryl pivalate split off at 120° C. within 1.5 hours 3.23 std. liters (144 mmoles) of 98% (MS) ethane. From the orange mixture are removed 20.8 g. (69.8 mmoles) of bis(ethylpivaloyloxy-boryl)-oxide by distillation. After admixture with 2 × 50 ml. of methanol and removal of all readily volatile constituents by distillation, 11.8 g. (64 mmoles) of 97% (GC) of yellow viscous E condensate are obtained.

Butyrophenone and benzaldehyde:

7.4 g. (50 mmoles) of butyrophenone, 7.5 g. (70.8 mmoles) of benzaldehyde, and 19.2 g. (112.8 mmoles) of diethyl boryl pivalate give after 1.5 hours a yellowish mixture from which 1.28 std.liters (57.1 mmoles) of 97% (MS) ethane have cleaved off. 14.5 Grams (48.6 mmoles) of bis(ethyl-pivaloyloxy-boryl)oxide are distilled off. After addition of 2 × 50 ml. of methanol, 11.2 g. (47 mmoles) of Z/E condensate (~1:1) (GC) are obtained.

Table 5

Cocondensation products C from benzaldehyde (B) and ketones (A) with a methylene or methyl group in alpha position (reaction type II).

| Ketone (A) | Yield (%) | Purity (%) | Characteristic | Consecutive No. |
|---|---|---|---|---|
| Methyl isopropyl ketone | 59 | 99 | liquid, yellowish | 21 |
| t-Butylmethyl ketone (Pinacoline) | 63 | 100 | solid, colorless m.p. 33 | 22 |
| acetophenone | 38° C. | | | |
| 2-Methyl cyclohexanone | 90 | 98 | viscous, yellow | 23 |
| 2-Cyclohexenone | 93 | 97 | viscous, yellow | 24 |
| 1-Indanone | 99 | 98 | solid, yellow m.p. 110° C. | 25 |
| 1-Tetralone | 96 | 97 | solid, yellow m.p., 96° C. | 26 |
| Dehydro-epi-androsterone | 96 | >95 | solid, colorless m.p., 164° C. | 27 |
| Acetophenone | 96 | 99 | solid, yellow m.p., 55° C. | 28 |
| Propiophenone | 96 | 99 | viscous, yellowish | 29 |
| Butyrophenone | 94 | 100 | viscous, yellowish | 30 |
| Valerophenone | 94 | 100 | viscous, yellowish | 31 |
| Caprophenone | 95 | 100 | viscous, yellowish | 32 |
| 2,4-Dimethyl- | 97 | 98 | viscous, yellow | 33 |
| 2-Chloroacetophenone | 96 | >95 | viscous, yellow-green | 34 |
| 2-Hydroxy-acetophenone | 88 | >95 | solid, brown powder | 35 |
| 4-Acetoxy acetophenone | 89 | >95 | solid, yellowish m.p., 60° C. | 36 |

2:1 Cocondensates of ketones having two alpha-methylene or alpha-methyl groups and benzaldehyde (see Table 6)
General procedure To a mixture of 30 to 80 mmoles of ketone and 100 to 400 mmoles of benzaldehyde are added dropwise while thoroughly stirring at about 120° C. 130 to 360 mmoles of diethyl boryl pivalate. While the mixture changes its color, 130 to 360 mmoles of ethane with at most 1 to 5 % of ethylene are evolved. After processing there are obtained (see above) 280 to 780 mmoles of condensation product and in addition 70 to 180 mmoles of bis(ethyl-pivaloyloxy-boryl)oxide.

Acetone and benzaldehyde

From 4.3 g. (74.2 mmoles) of acetone, 23 g. (217 mmoles) of benzaldehyde and 52 g. (306 mmoles) of diethyl boryl pivalate an orange mixture is obtained after 3 hours. 5.5 Std.liter (246 mmoles) of 95% (MS) ethane are split off. 36 Grams (120.5 mmoles) of bis-(ethyl-pivaloyloxyboro)oxide are distilled off. After having added 2 × 50 ml. of methanol, 14.5 g. (61.7 mmoles) of 98.5% (GC) orange, very viscous EE condensate are obtained.

Cyclopentanone and benzaldehyde

A mixture of 6.3 g. (75 mmoles) of cyclopentanone, 19.9 g. (187.5 mmoles) of benzaldehyde and 52.2 g. (307 mmoles) of diethyl boryl pivalate is heated in 100 ml. of toluene for 3 hours. After 6.6 Std. liters (295 mmoles) of pure (MS) ethane have split off, 42 g. (140.1 mmoles) of bis(ethylpivaloyoxyboro)oxide are distilled off. The yellow-orange residue is mixed with 2 × 50 ml. of methanol whereupon all readily volatile constituents are distilled off. After recrystallization from methanol, 17.2 g. (66 mmoles) of a pure (CC) yellow EE condensate having a melting point of 196° C. are obtained from 19.8 g. of raw condensate.

Table 6

| | 2:1 Cocondensate C of benzaldehyde B and ketones A having two methylene or methyl groups | | | |
|---|---|---|---|---|
| | | 2:1 Cocondensation product 37–42 | | |
| Ketone (A) | Yield (%) | Purity (%) | Characteristic | Consecutive No. |
| Acetone | 83 | 99 | viscous, orange | 37 |
| 2-Butanone | 81 (+10)* | 94 | viscous, orange | 38 |
| 3-Pentanone | 71 (+12)* | 96 | viscous, brown | 39 |
| Cyclopentanone | 88 | 100 | crystalline, needle-shaped, yellow m.p., 196° C. | 40 |
| Cyclohexanone | 95 | 99 | crystalline, yellow m.p., 107–113° C. | 41 |
| Cyclododecanone | 84 | >95 | viscous, yellow | 42 |

*1:1 condensate

Condensation by reaction type II from camphor (A) and different carbonyl compounds of the type B (see Table 7)
Camphor and fluorenone:

A mixture of 8 g. (52 mmoles) of camphor, 10.5 g. (58.3 mmoles) of fluorenone, and 22.8 g. (134 mmoles) of diethyl boryl pivalate is heated for 3 hours to 150° C. While the mixture assumes an orange color, 2.62 std.liters (117 mmole of pure (MS) ethane are split off. The readily volatile constituents among which are 14 g. (46.9 mmoles) of bis(ethylpivaloyloxyboro)oxide are distilled off under vacuum (to 95° C./0.1 Torr). 17 Grams of a yellow residue are mixed with 2 × 50 ml. of methanol and the boron-containing constituents and traces of pivalic acid are distilled off, finally under vacuum (bath of 100° C.) to give 15.5 g. (49.3 mmoles) of 99% (GC) yellow solid condensate having a melting point of 50° to 54° C.

Table 7

| Cocondensation products C from camphor (A) and carbonyl compounds (B) | | | | |
|---|---|---|---|---|
| | | Cocondensates 43–48 | | |
| Carbonyl compound (B) | Yield (%) | Purity (%) | Characteristic | Consecutive No. |
| Pivalaldehyde | 89 | 100 | liquid, colorless | 43 |
| 2-Adamantanone | 90 | 99 | solid, colorless m.p., 85° C. | 44 |
| Benzaldehyde | 92 | 100 | viscous, yellow | 45 |
| Benzophenone | 90 | 92 | solid, yellow m.p., 100–106° C. | 46 |
| Fluorenone | 94 | 99 | solid, yellow m.p., 50–54° C. | 47 |
| Chalcone | 92 | 92 | solid, yellow m.p., 110–112° C. | 48 |

Condensation by reaction type II of different carbonyl compounds A and B (see Tables 8 to 10)
General procedure To a mixture of 0.2 to 0.6 moles of carbonyl compound of type B and 0.2 mole (per mole of alpha-$CH_2$ in A) of diethyl boryl pivalate is added dropwise at 80°–120° C., a mixture of 0.1 mole of carbonyl compound type A and carbonyl compound type B. For each alpha-$CH_2$ group of A are formed 0.2 mole of ethane and 0.1 mole of bis[ethyl-pivaloyloxoboro]oxide. After having distilled off the excess B and the oxide, the compound C is obtained almost quantitatively as residue.

Table 8

Cocondensation products (C) 49 to 54 from different aldehydes (A) and (B)

| Aldehyde A | B | Condensation products C |  |  |  |
|---|---|---|---|---|---|
|  |  | Yield[a] (%) | Purity (%) | Characteristic | No. |
| Acetaldehyde | Benzaldehyde | 80 | 95 | yellow, liquid | 49 |
| Propanal | Benzaldehyde | 78 | 95 | yellow, liquid | 50 |
| Butanal | Benzaldehyde | 75 | 95 | yellow, viscous | 51 |
| Capronaldehyde | Benzaldehyde | 68 | 95 | yellow, viscous | 52 |
| 1-Valerialdehyde | Benzaldehyde | 74 | 95 | yellow, viscous | 53 |
| 2-Ethylbutanal | Benzaldehyde | 79 | 95 | yellow, viscous | 54 |

[a] The balance consists of higher condensation products.

Table 9

Cocondensation products (C) 55 to 64 from different ketones (A) and aldehydes (B)

| Carbonyl compound A | B | Condensation products C |  |  |  |
|---|---|---|---|---|---|
|  |  | Yield (%) | Purity (%) | Characteristic | No. |
| 1-Indanone | Paraformaldehyde | 85 | 95 | yellowish, liquid | 55 |
| 1-Tetralone | Paraformaldehyde | 89 | 90 | yellowish, liquid | 56 |
| Camphor | Paraformaldehyde | 87 | 90 | colorless, liquid | 57 |
| 1-Indanone | Pivaldehyde | 91 | 95 | yellow, viscous | 58 |
| Propiophenone | Pivaldehyde | 85 | 95 | yellow, viscous | 59 |
| Dimedone | Benzaldehyde | 84 | 90 | red, viscous | 60 |
| Progesterone | Benzaldehyde | 98 | 95 | yellow, solid | 61 |
| Propiophenone | 4-Hydroxy-benzaldehyde[a] | 95 | 95 | yellow, viscous | 62 |
| Propiophenone | 3-Hydroxy-benzaldehyde[a] | 94 | 95 | yellow, viscous | 63 |
| Propiophenone | 4-Amino-benzaldehyde[a] | 96 | 95 | yellow, viscous | 64 |

[a] Per mole of OH- or NH$_2$ group, 1 mole of diethylboryl pivalate is additionally used and slowly added to the aldehyde at 80° C. Thereafter, the reaction is carried out as described.

Table 10

Cocondensation products (C) 65 to 72 from different ketones (A) and (B)

| Ketone A | B | Condensation products C |  |  |  |
|---|---|---|---|---|---|
|  |  | Yield (%) | Purity (%) | Characteristic | No. |
| Acetophenone | Benzophenone | 85 | 96 | orange, viscous | 65 |
| Indanone | Benzophenone | 92 | 98 | yellow, viscous | 66 |
| Cyclohexanone | Benzophenone | 93 | 97 | yellow, viscous | 67 |
| Pinacoline | Benzophenone | 91 | 97 | yellow, viscous | 68 |
| Acetone | Benzophenone | 92 | 96 | yellow, viscous | 69 |
| Acetone | Chalcone | 90 | 92 | orange, viscous | 70 |
| Acetone | Fluorenone | 86 | 97 | orange, solid | 71 |
| 2-Methyl-cyclohexanone | Fluorenone | 85 | 96 | yellow, solid | 72 |

Homocondensation by means of different dialkyl boryl carboxylate

To 120 mmoles of carbonyl compound (A) is added dropwise at 100°-110° C. within about 1 hour a solution of 120 mmoles of dialkyl boryl carboxylate in 150 ml. of toluene. Thereby, 115-120 mmoles of ethane are liberated. After having distilled off the toluene under vacuum, about 60 mmoles of bis(alkyl-carboxyloxy)-diboroxane (boiling range, 70°-95° C./0.1 Torr) are obtained. The residue is mixed with 250 ml. of methanol and all of the readily volatile constituents are distilled off to give 52 to 59 mmoles (87-99%) of condensate C (see Table 11).

Table 11

Homocondensation by means of different dialkyl boryl carboxylate

| Carbonyl compound | Condensing agent | Yield (%) | Purity (%) | No. |
|---|---|---|---|---|
| Propiophenone | Diethylboryl acetate | 91 | 96 | 2 |
| Caprophenone | Diethylboryl acetate | 89 | 97 | 5 |
| Cyclododecanone | Diethylboryl acetate | 92 | 95 | 11 |
| Propiophenone | Diethylboryl propionate | 93 | 97 | 2 |
| Cyclooctanone | Diethylboryl propionate | 91 | 96 | 10 |
| Propiophenone | Diethylboryl-cyclopropane carboxylate | 92 | 98 | 2 |
| Cyclododecanone | Diethylboryl-cyclopropane carboxylate | 90 | 96 | 11 |
| Propiophenone | Diethylboryl benzoate | 90 | 97 | 2 |
| Cyclooctanone | Diethylboryl benzoate | 89 | 98 | 10 |
| Propiophenone | Dipropylboryl pivalate | 97 | 96 | 2 |

Table 11-continued

| Homocondensation by means of different dialkyl boryl carboxylate | | | | |
|---|---|---|---|---|
| Carbonyl compound | Condensing agent | Yield (%) | Purity (%) | No. |
| Cyclooctanone | Dipropylboryl pivalate | 94 | 95 | 10 |

Cocondensation by means of different dialkylboryl carboxylates:

To a mixture of 50 mmoles of carbonyl compound (A) and about 150 mmoles of carbonyl compound (B) is added dropwise at 100° to 110° C. within about 1 hour a solution of 100 mmoles of dialkylboryl carboxylate in 150 ml. of toluene. About 100 mmoles of ethane are liberated. After having distilled off toluene and excess compound B, about 50 mmoles of bis(alkylcarboxyloxy)diboroxane (boiling range, 70°–95° C./0.1 Torr) are obtained. The residue is mixed with 250 ml. of methanol and the readily volatile constituents are distilled off to give 42–48 mmoles (84–96%) of condensate (see Table 12).

Table 12

| Cocondensation of A and B by means of different dialkyl boryl carboxylates | | | Condensate C | | |
|---|---|---|---|---|---|
| Carbonyl compound | | | Yield | Purity | |
| A | B | Condensing agent | (%) | (%) | No. |
| Cyclohexenone | Benzaldehyde | Diethylboryl acetate | 92 | 96 | 24 |
| Butanal | Benzaldehyde | Diethylboryl acetate | 67 | 92 | 51 |
| Pinacoline | Benzaldehyde | Diethylboryl acetate | 94 | 93 | 22 |
| 1-Tetralone | Benzaldehyde | Diethylboryl propionate | 92 | 95 | 26 |
| Isophorone | Benzaldehyde | Diethylboryl propionate | 83 | 94 | 73 |
| 1-Indanone | Benzaldehyde | Diethylboryl cyclopropane carboxylate | 94 | 96 | 25 |
| 2-Methylcyclohexanone | Benzaldehyde | Diethylboryl cyclopropane carboxylate | 91 | 97 | 23 |
| 1-Tetralone | Benzaldehyde | Diethylboryl benzoate | 93 | 94 | 26 |
| Methylisopropyl ketone | Benzaldehyde | Diethylboryl benzoate | 50 | 95 | 21 |
| 1-Indanone | Benzaldehyde | Dipropylboryl pivalate | 95 | 96 | 25 |
| Pinacoline | Benzaldehyde | Dipropylboryl pivalate | 97 | 95 | 22 |
| Propiophenone | Benzaldehyde | Dipropylboryl pivalate | 96 | 98 | 29 |

SUMMARY

Thus, the invention is concerned with a process for producing condensates wherein the following overall reaction is carried out:

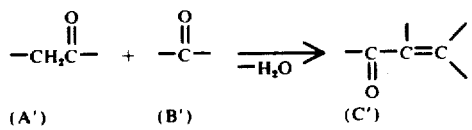

The invention provides the improvement which comprises carrying out said reaction in the presence of a dialkyl boryl carboxylate of the formula

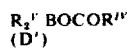

wherein
R$^{IV}$ is C$_1$–C$_8$ hydrocarbon, and
R$^V$ is each C$_1$–C$_4$ hydrocarbon.

R, R', R'' and R''' can be of any size. In general they will be C$_1$ to C$_{30}$, and preferably are C$_1$–C$_{18}$. As noted above, R, R', R'' and R''' can be linked in various ways. Where the said substituents are linked, the resulting chains of the two substituents can contain C$_5$–C$_{20}$ carbon atoms. As noted above R$^{IV}$ and R$^V$ are hydrocarbons, which can be saturated or unsaturated, e.g. olefinically unsaturated; they can be e.g. alkyl, alkylene, cycloalkyl, unsaturated cycloalkyl, or aryl.

The products according to the invention, as is well known, are useful for various purposes, for example in the production of polymeric colored oils and resins; as intermediates for the production of diols and dions which, for instance, are useful for polymerizations and oligomerizations; intermediates for complex components of various metal compounds; intermediates for the production of hydrocarbons otherwise accessible only with difficulty, by, for example reduction of materials produced according to the invention. Additionally, the process of the invention is useful for the introduction of certain functions at certain locations in the molecule, i.e. of keto-functions in α-position to original carbonyl functions. Also intermediates for the production of detergents can be produced.

The process is generally applicable to aldol condensations and thus can be used to make the myriad of known products, having known uses, produced by that reaction. The acrolein will at least partly react further as indicated at page 4, line 11–14. The invention can be used for production of benzalacetone by condensation of acetone and benzaldehyde; benzalacetophenone by condensation of acetophenone and benzaldehyde; phenylpropenal by condensation of benzaldehyde and acetaldehyde; 1,5-diphenyl-1,3,5-pentadienone (dibenzalacetone) from condensate from benzaldehyde and acetone; 2-(cyclo-1-hexenyl)cyclohexanone from cyclohexanone and isomerization; and 2-cyclohexylcyclohexanol from cyclohexanone and following reduction.

What is claimed is:

1. In the aldol condensation reaction wherein a ketone or aldehyde group having an alpha methylene group is reacted with a ketone or aldehyde group to form an alpha-, beta-unsaturated ketone or aldehyde, the improvement which comprises carrying out said reaction in the presence of a dialkyl boryl carboxylate of the formula:

wherein
  $R^{IV}$ is $C_1$–$C_6$ hydrocarbon and
  $R^V$ is each $C_1$–$C_4$ alkyl.

2. Process according to claim 1, wherein the ketone or aldehyde group having an alpha methylene group is contained in a compound of the formula:

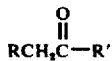

and the other ketone or aldehyde group is contained in a compound of the formula:

wherein:
  R, R',R", and R'" is each hydrogen, alkyl, or aryl, and R and R' can be linked together to form a ring, and R" and R'" can be linked together to form a ring, and R' and R'" can be linked together, and R' and R" can be linked together.

3. Process according to claim 1, wherein the ketone or aldehyde group having an alpha methylene group is contained in a compound of the formula:

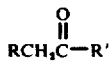

and the other ketone or aldehyde group is contained in a compouund of the formula:

wherein:
  R, R',R", and R'" is each hydrogen, alkyl, or aryl, and R and R' can be linked together to form a ring, and R" and R'" can be linked together to form a ring.

4. Process according to claim 1, wherein the dialkyl boryl carboxylate is diethyl boryl pivalate.

5. Process according to claim 1, wherein the dialkyl boryl carboxylate is at least one of:
  diethylboryl acetate
  diethylboryl propionate
  diethylboryl-cyclopropane carboxylate
  diethylboryl benzoate
  dipropylboryl pivalate
  diethylboryl pivalate.

6. Process according to claim 1, wherein said temperature is 20°–150° C.

7. Process of claim 2, wherein the dialkyl boryl carboxylate is diethyl boryl pivalate.

8. Process of claim 6, wherein the dialkyl boryl carboxylate is diethyl boryl pivalate.

* * * * *